(12) United States Patent
Marshall et al.

(10) Patent No.: US 10,891,590 B2
(45) Date of Patent: *Jan. 12, 2021

(54) PET INSURANCE SYSTEM AND METHOD

(71) Applicant: Trupanion, Inc., Seattle, WA (US)

(72) Inventors: Kerri E. Marshall, Seattle, WA (US); Darryl Rawlings, Seattle, WA (US); Kathryn Plowman, Portland, ME (US); Christopher Cappelletti, Carnation, WA (US)

(73) Assignee: Trupanion, Inc., Seattle, WA (US)

( * ) Notice: Subject to any disclaimer, the term of this patent is extended or adjusted under 35 U.S.C. 154(b) by 120 days.

This patent is subject to a terminal disclaimer.

(21) Appl. No.: 14/210,079

(22) Filed: Mar. 13, 2014

(65) Prior Publication Data

US 2014/0278551 A1 Sep. 18, 2014

Related U.S. Application Data

(60) Provisional application No. 61/801,404, filed on Mar. 15, 2013.

(51) Int. Cl.
*G16H 40/20* (2018.01)
*G06Q 10/10* (2012.01)
*G06Q 40/08* (2012.01)

(52) U.S. Cl.
CPC .......... *G06Q 10/10* (2013.01); *G06Q 40/08* (2013.01); *G16H 40/20* (2018.01)

(58) Field of Classification Search
CPC ......... A61B 90/90; A61B 90/94; G16H 40/20
See application file for complete search history.

(56) References Cited

U.S. PATENT DOCUMENTS

| | | | |
|---|---|---|---|
| 5,720,502 A | 2/1998 | Cain | |
| 6,117,526 A | 9/2000 | Marks | |
| 6,966,064 B1* | 11/2005 | Schneidewend ... | H04N 5/44543 348/E5.105 |
| 7,155,405 B2 | 12/2006 | Petrovich | |
| 7,266,770 B2 | 9/2007 | Onbe et al. | |
| D572,717 S | 7/2008 | Loehr et al. | |
| 7,496,583 B2 | 2/2009 | Moore et al. | |
| D605,653 S | 12/2009 | Danton | |
| 7,711,660 B1 | 5/2010 | Gentile et al. | |
| 8,341,547 B2 | 12/2012 | Ingman et al. | |

(Continued)

FOREIGN PATENT DOCUMENTS

| | | |
|---|---|---|
| JP | 2002-073802 | 3/2002 |
| JP | 2013-022984 | 2/2013 |

(Continued)

OTHER PUBLICATIONS

PCT International Search Report of PCT/US14/27042; dated Oct. 1, 2014; (4 pgs.).

(Continued)

*Primary Examiner* — Reginald R Reyes
(74) *Attorney, Agent, or Firm* — Wilson Sonsini Goodrich & Rosati

(57) ABSTRACT

A pet insurance system and method are provided. The pet insurance system provides rapid insurance enrollment and quick claim processing. In addition, the pet insurance system and method generates a pet health status identifier that is displayed to users of the system.

3 Claims, 15 Drawing Sheets

(56) References Cited

U.S. PATENT DOCUMENTS

| | | | |
|---|---|---|---|
| 8,359,605 B2 | 1/2013 | Ross | |
| D777,737 S | 1/2017 | Marshall et al. | |
| 10,013,530 B2 | 7/2018 | Marshall et al. | |
| 10,255,993 B2 | 4/2019 | Marshall et al. | |
| 2002/0099276 A1* | 7/2002 | Schmidt | A61B 5/16 600/300 |
| 2003/0004740 A1 | 1/2003 | Dickey et al. | |
| 2004/0254816 A1 | 12/2004 | Myers | |
| 2005/0060344 A1* | 3/2005 | Pawlick | A01K 11/008 |
| 2005/0091606 A1 | 4/2005 | Sauermann | |
| 2006/0074724 A1* | 4/2006 | Schwartz | G06Q 50/24 705/4 |
| 2006/0075724 A1 | 4/2006 | Kammler et al. | |
| 2006/0196436 A1 | 9/2006 | Nichols | |
| 2006/0251775 A1 | 11/2006 | Anderson et al. | |
| 2007/0084099 A1 | 4/2007 | Sarbo et al. | |
| 2007/0203758 A1* | 8/2007 | Stephens | G06Q 40/08 705/4 |
| 2008/0172617 A1 | 7/2008 | Takeda et al. | |
| 2008/0307339 A1 | 11/2008 | Boro et al. | |
| 2009/0106678 A1 | 4/2009 | Chase et al. | |
| 2009/0182586 A1* | 7/2009 | Cohane | G06Q 30/0225 705/4 |
| 2009/0289844 A1 | 11/2009 | Palsgrove et al. | |
| 2009/0300540 A1 | 12/2009 | Russell | |
| 2010/0017234 A1 | 1/2010 | Stephens et al. | |
| 2010/0293487 A1 | 11/2010 | Schoenberg | |
| 2011/0119574 A1 | 5/2011 | Rogers et al. | |
| 2011/0131507 A1 | 6/2011 | Butcher | |
| 2012/0060105 A1 | 3/2012 | Brown et al. | |
| 2012/0060216 A1 | 3/2012 | Chaudhri et al. | |
| 2012/0110453 A1 | 5/2012 | Ma et al. | |
| 2012/0265702 A1* | 10/2012 | Maher | G06Q 10/10 705/317 |
| 2013/0073366 A1* | 3/2013 | Heath | G06Q 30/0261 705/14.25 |
| 2013/0218592 A1* | 8/2013 | Hashmat | G16H 40/20 705/3 |
| 2014/0155785 A1* | 6/2014 | Haas | A61B 5/1038 600/595 |
| 2016/0364547 A1* | 12/2016 | Love | G06F 19/3456 |
| 2018/0349852 A1 | 12/2018 | Marshall et al. | |

FOREIGN PATENT DOCUMENTS

| | | |
|---|---|---|
| WO | WO-2006036316 A1 | 4/2006 |
| WO | WO-2014152179 A2 | 9/2014 |
| WO | WO-2017075207 A1 | 5/2017 |

OTHER PUBLICATIONS

PCT Written Opinion of the International Searching Authority of PCT/US14/27042; dated Oct. 1, 2014; (7 pgs.).

Co-pending U.S. Appl. No. 16/023,624, filed Jun. 29, 2018.

European search report dated Dec. 9, 2016 for EP Application No. 14770490.

International search report with written opinion dated Nov. 29, 2016 for PCT/US2016/059095.

Notice of allowance dated May 17, 2018 for U.S. Appl. No. 14/924,606.

Notice of allowance dated May 29, 2018 for U.S. Appl. No. 14/924,606.

U.S. Appl. No. 14/924,606 Final Office Action dated Jul. 22, 2016.

U.S. Appl. No. 14/924,606 Final Office Action dated Oct. 12, 2017.

U.S. Appl. No. 14/924,606 Non-Final Office Action dated Jan. 12, 2017.

U.S. Appl. No. 14/924,606 Non-Final Office Action dated Mar. 10, 2016.

U.S. Appl. No. 29/449,619 Final Office Action dated Jul. 17, 2015.

U.S. Appl. No. 29/449,619 Non-Final Office Action dated Oct. 3, 2014.

U.S. Appl. No. 29/449,619 Notice of Allowance dated Sep. 13, 2016.

2011 Trupanion set up: pp. 15 to 17 https://mc9ljrfyiceiaeu2gdfotgw0-wpengine.netdna-ssl.com/wp-content/uploads/2019/09/AVImark-Release-Notes-2011.3.6.pdf, 25 pages.

2012 1st Annual Naphia Conference. Vetenvoy featured presenter. ("1st annual naphia summit_VE Described_Copied for Patent.pdf") 7 pages.

2012 ACT, Sep. 2008 PurinaCare. ("ACT Automated Claims Processing Feb. 2012 Proposal.doc") 9 pages.

Avimark 2011 announcement of offering ("Avimark_2011-Insurance Update.pdf") 1 page.

Avimark, ("Avimark-Release-Notes-2011.3.6.pdf") https://docplayer.net/63752091-Avimark-readme-table-of-contents-please-use-the-bookmark-menu-on-the-left-to-navigate-between-each-project-and-feature-1.html, 21 pages (accessed on Apr. 15, 2020).

Avimark, http://docplayer.net/11571437-Vpi-eclaim-equote-integration.html, 18 pages (accessed on Apr. 15, 2020).

Avimark Insurance and vetenvoy, https://www.petinsurance.com/images/VSSimages/landingPages/Vet_Envoy_AVImark/setup.pdf, 3 pages (accessed on Apr. 15, 2020).

"AVImark eClaims Instructions v2.0 for Trupanion.pdf", 22 pages (2012).

PracticeOn: https://cdn.website-editor.net/f8ec393e8489444b912f11c22465414a/files/uploaded/Connector%2520v101%2520Insurance%2520Trials%2520Submission%2520Instructions%2520for%2520AVImark.pdf https://cdn.website-editor.net/f8ec393e8489444b912f11c22465414a/files/uploaded/Connector%2520v101%2520Insurance%2520Trials%2520Submission%2520Instructions%2520for%2520AVImark.pdf, 7 pages (2018).

PracticeOn in the market in Canada. https://www.practiceon.com/connector-insurance-support, 2 pages (2019).

Request for Ex Parte Reexamination filed Mar. 2, 2020 (56 pages) for U.S. Appl. No. 90/020,134 by PracticeOn Limited.

Trupanion_Avimark_PracticeOn 2011 Flyer.https://drive.google.com/file/d/1DNh3EVeoUwXaeh3-rfsTIvxdppDXhiHj/view?ts=5e587265 ("Trupanion_Avimark_Vetenvoy Practice Flyer.pdf") 1 page.

Vetenvoy / Livetime 24/7 Public and Open Api, Feb. 12, 2008 ("Vet Envoy Services API v1.50.pdf") http://www.vetenvoy.com/uk/content/vet%20envoy%20services%20api%20v1.50.pdf, 109 pages.

Vetenvoy's architecture, design and workflows. ("VE IT Topology.pdf") 5 pages (accessed on Apr. 15, 2020).

Vetenvoy in the press example, Dec. 2009 http://www.vetenvoy.com/uk/Content/VetEnvoy%20VBJ%20article.pdf, 4 pages.

Vetenvoy publicly shared information, Apr. 2009. https://veterinary-practice.com/article/a-giant-step-towards-the-paperless-office, 7 pages.

Vetenvoy.com information about eclaims, 2009. http://www.vetenvoy.com/,http://www.vetenvoy.com/, 2 pages.

Vetmessenger on 350+ practices 2012/13+ https://vimeopro.com/4act/vetenvoy-messenger-client-software/video/66664634, 1 page.

Vetmessenger on 350+ practices 2012/13+ https://www.dropbox.com/s/pddxa0ecflrcch1/New%20Development%2004.23.2013%20VetMessenger.mp4?dl=0, 1 page.

VetXML Consortium ("vetxml_timeline page.docx") http://www.vetxml.co.uk/en/about-the-consortium/#about-the-consortium, 7 pages (2020).

Co-pending U.S. Appl. No. 16/779,338, filed Jan. 31, 2020.

Notice of allowance dated Nov. 28, 2018 for U.S. Appl. No. 16/115,446.

U.S. Appl. No. 16/023,624 Non-Final Office Action dated Oct. 31, 2019.

AVImark, now Covetrus Software Services, AVImark Release Notes 2011.1.7, 75 pages https://softwareservices.covetrus.com/avimark-legacy-release-notes/, 2011.

Co-pending U.S. Appl. No. 16/941,483, inventors Marshall; Kerri E. et al., filed Jul. 28, 2020.

U.S. Appl. No. 16/023,624 Notice of Allowance dated Oct. 15, 2020.

Wikipedia, https://en.wikipedia.org/w/index.php?title=Plug_and_play&oldid=539757675, Plug and Play, Feb. 22, 2013.

(56) References Cited

OTHER PUBLICATIONS

U.S. Appl. No. 16/023,624 Notice of Allowance dated Feb. 21, 2020.
U.S. Appl. No. 16/023,624 Notice of Allowance dated Jul. 15, 2020.
U.S. Appl. No. 16/023,624 Notice of Allowance dated May 15, 2020.
U.S. Appl. No. 16/779,338 Office Action dated May 28, 2020.

* cited by examiner

PET INSURANCE SYSTEM AND METHOD

PRIORITY CLAIMS/RELATED APPLICATIONS

This application claims priority to and the benefit under 35 USC 119(e) and 120 of U.S. Patent Application Ser. No. 61/801,404, filed on Mar. 15, 2013 and entitled "Pet Insurance System and Method", the entirety of which is incorporated herein by reference.

FIELD

The disclosure relates generally to a pet insurance system and method.

BACKGROUND

Pet insurance has existed for a very long time since pets often have health problems that require major surgeries, treatment and the like. However, most current pet insurance systems are very cumbersome and do not allow a pet owner to rapidly obtain the insurance. Furthermore, most of the existing systems do not provide a veterinarian or pet hospital with an easy to view status of any particular pet so that the veterinary may not know, at the time of a major surgery or treatment, if the pet is going to be covered by insurance which would be desirable. In addition, most existing pet insurance systems take so long to process a claim that both the pet owner and the veterinarian or pet hospital are unhappy with the delay.

Thus, it is desirable to provide a pet insurance system and method that overcomes the above limitations and it is to this end that the disclosure is directed.

BRIEF DESCRIPTION OF THE DRAWINGS

FIG. 13 illustrates an example of a claims submission user interface of the pet insurance system; and FIGS. 14A and 14B are examples of a new claims and claim payment user interface of the pet insurance system.

DETAILED DESCRIPTION OF ONE OR MORE EMBODIMENTS

The disclosure is particularly applicable to a client server architecture pet insurance system and it is in this context that the disclosure will be described. It will be appreciated, however, that the system and method has greater utility.

Figure 1:
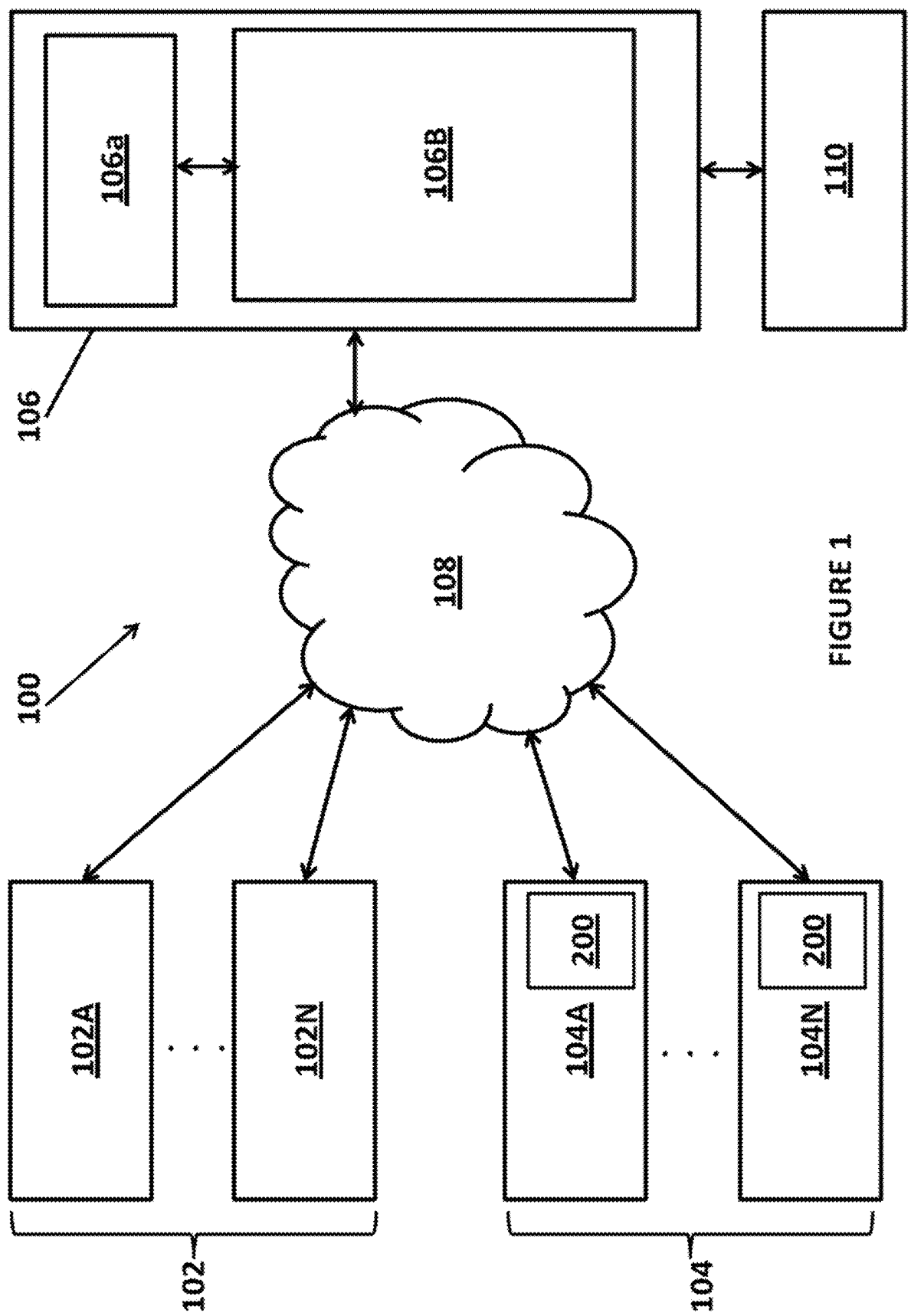
FIG. 1 is a diagram of an implementation of a pet insurance system.

FIG. 1 is a diagram of an implementation of a pet insurance system 100. The implementation in FIG. 1 is a typical client/server architecture that is described below in more detail. However, the system may also be implemented in a cloud computing architecture, a mainframe architecture, a software as a service mode and the like that are all which are within scope of this disclosure. The system may include one or more computing devices 102, such as 102A, . . . , 102N, and each computing device 102 may be used by a pet owner to connect to and interact with a pet insurance backend component 106 over a communications path 108. The system may also have one or more computing devices 104, such as 104A, . . . , 104N, and each computing device 104 may be used (or integrated into) a veterinary practice or pet hospital and allow the veterinary practice or pet hospital to connect to and interact with a pet insurance backend component 106 over a communications path 108. Each computing device 102, 104 may be a processor based device with storage, memory, a display and wireless or wired connectivity circuits that allow the computing device 102, 104 to interact with the backend component 106. For example, each computing device may be a smartphone device, such as a device operating using the iOS, Android or Symbian operating systems, a personal computer, a client server system, a terminal, a tablet computer, a cellular phone and any other device that would be capable of interacting with the backend component 106. In one implementation, each of the computing device 104 may have a client 200 that interacts with the backend component. In one implementation, the client or browser 200 may be a plurality of lines of computer code executed by the processor of the computing device. In one implementation, each of the computing device 102 may have a browser that interacts with the backend component, displays web pages and allows the user to enter information into forms. In one implementation, the browser may be a plurality of lines of computer code executed by the processor of the computing device 102.

The communication path 108 may be a wired or wireless network that may be unsecure or secure and uses typical protocols for the exchange of data between the computing devices 102, 104 and the backend component 106. For example, the communication path 108 may be an Ethernet network, the Internet, a wireless cellular network, a wireless digital data network and the like and the system is not limited to any particular communication path 108. In the implementation in which the communication path 108 is the Internet, the communication path 108 may use the known HTTP or HTTPS protocol for data communications.

The backend component 106 may be implemented as one or more computing resources or hardware devices. In one implementation, the backend component 106 may be one or more server computers, one or more cloud computing resources and the like and each resource has one or more processors, memory, persistent storage and the like. The backend component 106 may further comprise a web server 106a, a pet insurance management component 106B and a storage device 110 that are coupled together as shown in FIG. 1. The web server 106a, that may be implemented as a hardware web server or a software implemented web server, may generate and exchange web pages with each computing device 102 and exchange data with each computing device 102 that is using a browser. The pet insurance management component 106B manages the pet insurance system operations, including enrollment of pet owners, generation and maintenance of a status of each pet in the system, payment and processing of claims from the pet owners and interactions with the veterinary practice or pet hospital. The pet insurance management component 106B may be implemented as a plurality of lines of computer code that are stored in the computing resources and then executed by the processor(s) of the computing resources to implement the pet insurance management functions that are described below in more detail. The storage device 110 may be a hardware storage device or a software implemented storage device such as a database, that stores user and veterinary practice or pet hospital information for the system, stores information about each pet that is enrolled in the pet insurance system and stores the information about each pet insurance claim in the system.

Figure 2:
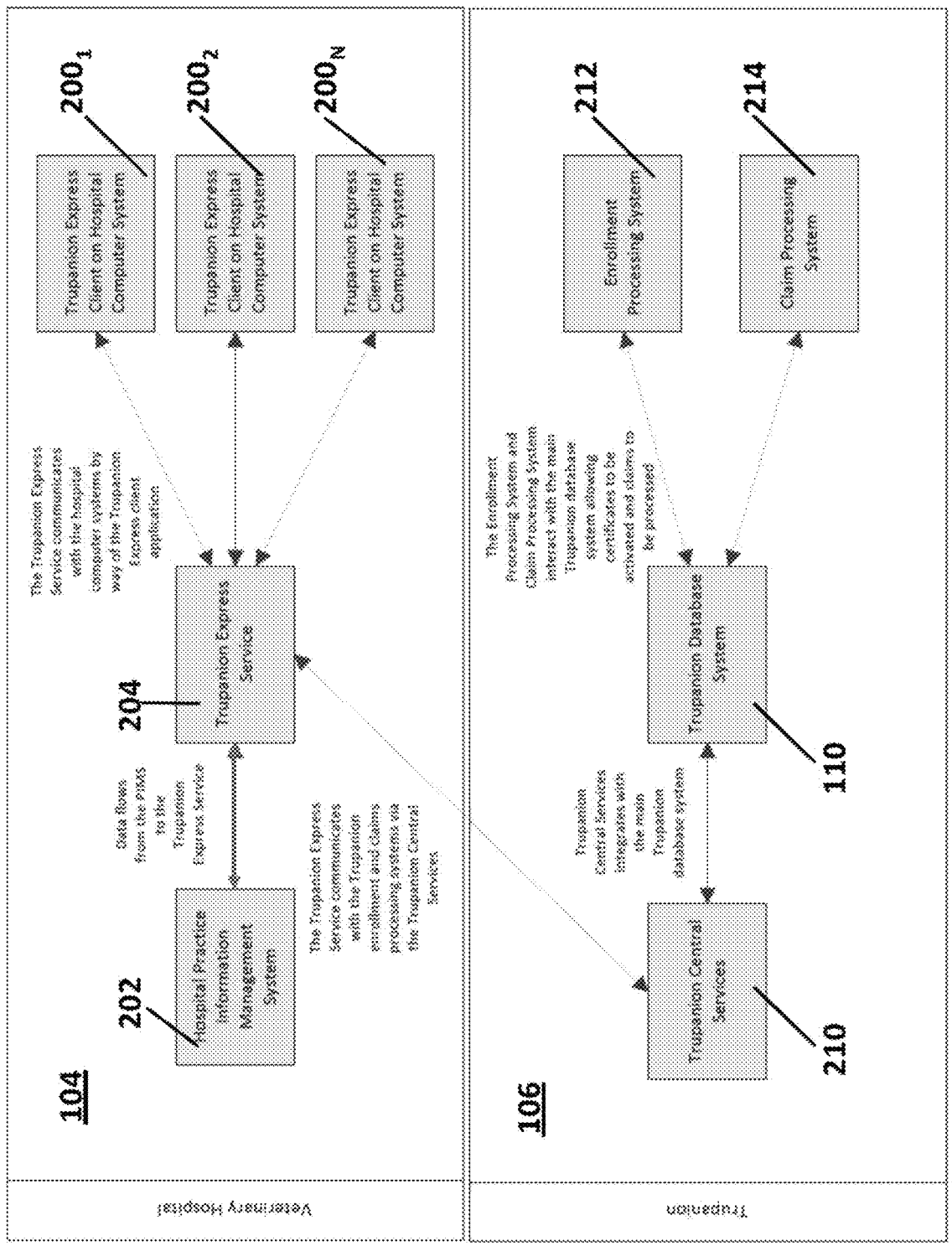
FIG. 2 illustrates more details of the pet insurance system.

FIG. 2 illustrates more details of the pet insurance system and in particular the components in each veterinary practice or pet hospital computing device 104 and the backend component 106 and the interactions between the two. As shown, the veterinary practice or pet hospital may have one or more clients 200, a hospital information management system 202 and a pet insurance component 204. As shown, data from the hospital information management system 202 flow into the pet insurance component 204 and the pet insurance component 204 connects to and communicates with the backend component 106 (specifically an enrollment system and a claims processing system) and the pet insurance component 204 connects to and communicates with the one or more clients 200 in the computing devices 104. In one implementation, each of the components of the veterinary practice or pet hospital computing device 104 may be a plurality of lines of computer code that are executed by a processor of the computing device 104. The Hospital Practice Information Management System (PIMS) is an existing system used by a veterinary practice or pet hospital that use database and visualization technologies (user interface) with the aim to support various hospital/patient management and administration tasks. Different PIMS manufacturers include different modules that allow for many common hospital technology requirements that may include inventory tracking, procedure codes, connection to diagnostic equipment and service providers, connection to a variety of radiology modalities and services and invoice generation.

The pet insurance component 204 may be provided by the pet insurance backend system 106 and may be installed in the computing device 104 of the veterinary practice or pet hospital. The pet insurance component 204, that may be known as the Trupanion Express service (TES), is a system which integrates with these varied systems to provide added value and operational simplicity for both veterinarians and pets. The service component of TES is responsible for retrieving and mapping data from any PIMS, communicating with Trupanion Central Services (TCS) 210 about claims or certificates and communicating with Trupanion Express Client (TREX) 200. TES 204 employs various technological mechanisms to reduce the amount of traffic between TCS and TREX, as well as the PIMS creating efficient correspondence. TES 204 may include an abstracted engine that allows communication with various PIMS systems on market today, as well as the ability to integrate with more in the future in a plug-and-play fashion.

The client 200, that may be known as Trupanion Express Client (TREX), is the user interface for Trupanion Express. It communicates with TES 204 with the aim to exchange information between the hospital and the backend component 106. The client allows submitting claims, issuing certificates, searching PIMS data for pet insurance clients and appointments, mapping clients between systems, and displaying all of the information for these activities in a digestible way for hospital staff. Additionally, TREX 200 is a catalyst for better workflows and communications for hospital staff—resulting in significantly improved patient care.

The backend component 106 may further comprise a services component 210, that may be known as Trupanion Central Services, the storage device 110, known as Trupanion database system, an enrollment processing system 212 and a claim processing system 214 that are coupled to each other as shown in FIG. 2. Sample data is included in the below table:

| Sample Data Exchanged Between the Hospital & Trupanion | Enrollment Sample Data | Claims Sample Data |
| --- | --- | --- |
| Patient Demographics | Policy ID & Type | Claim Basics |
| Client Demographics | Policy Status | Claiming Clinic |
| Claim Form Information | Enrollment Clinic Information | Information |
| Invoices/Estimates | Policy Coverage Details | Claim Outcomes & Amount Covered |
| Medical Record Information | | |
| Certificates Status | | |

In one implementation, each of the components of the backend component 106 may be a plurality of lines of computer code that are executed by a processor of the computing device 106. The services component 210 integrated with the storage device. The enrollment processing system 212 and a claim processing system 214 may interact with the storage 110 allowing certificates to be issued and activated and claims to be processed. The services component 210 is a service inside Trupanion's network that receives TES requests and passes the appropriately-formed requests on to the Trupanion Database System (TruDat) 110. The Trupanion Database System (TruDat) is any location where transactional data for Trupanion's various IT systems is stored. The Enrollment Processing System is the system that issues certificates to pet owners interested in potentially becoming a Trupanion policyholder and the claim Processing System (PO) is the system that catalogs the collection of medical records that enables claims adjudicators to manage and process pet owner claims. Trupanion Express is revolutionary in that one of its purposes is to allow claims to be adjudicated very quickly—allowing the pet owner to not pay out-of-pocket expenses at the veterinary hospital. Said another way, Trupanion Express allows Trupanion to pay veterinarians directly with PO while the customer is standing at checkout, similar to the concept of a "co-pay" in human health care. Trupanion Express allows for near real time claims submission and claims processing enabling claim adjudication at point of sale at the veterinary clinic. Versus typical channels such as fax or mail that support a delayed reimbursement model for veterinary practices or pet hospitals and/or pet owners. For additional details, see Claim A.

Figure 3:
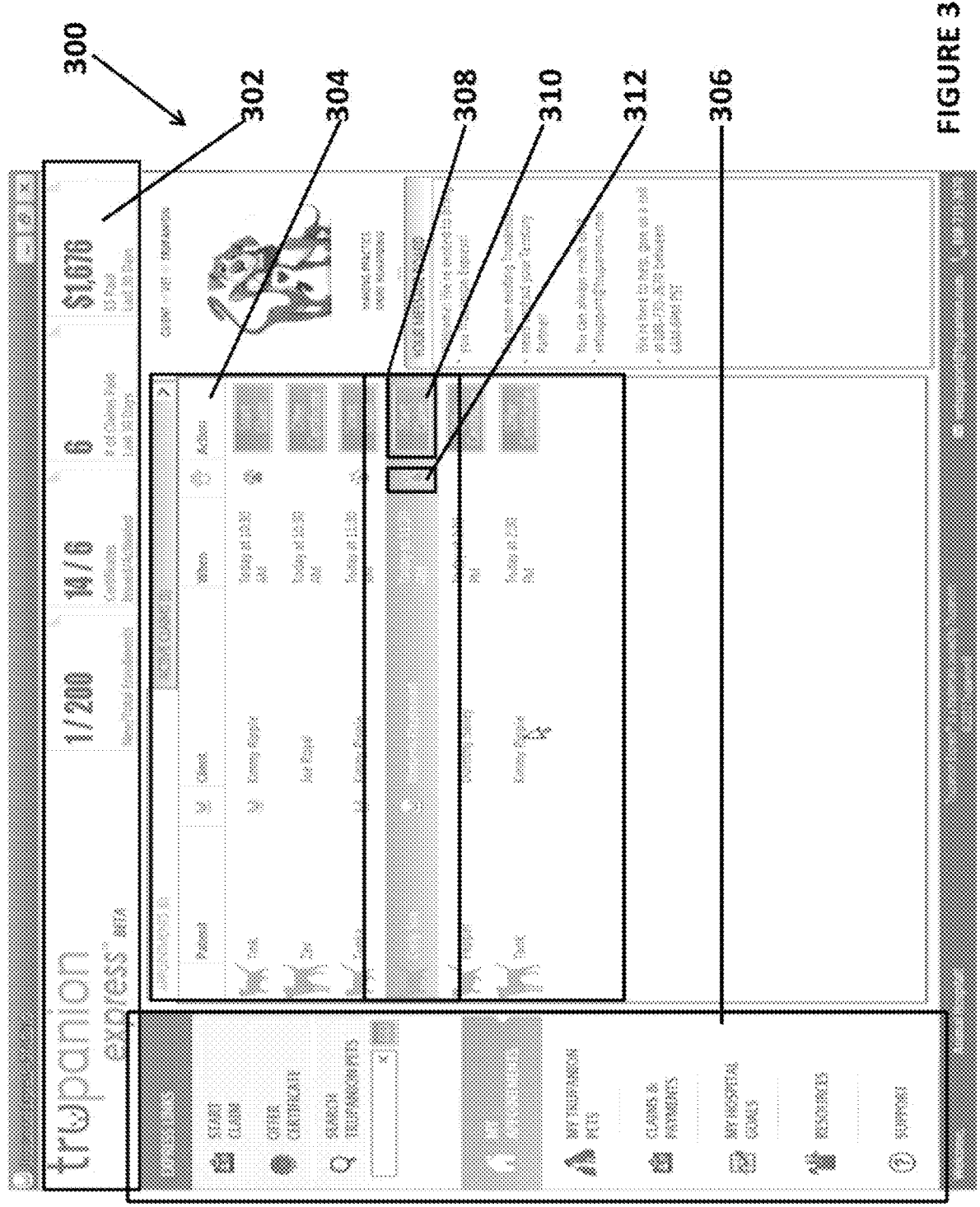
FIG. 3 illustrates an example of a user interface of the pet insurance system.

FIG. 3 illustrates an example of a user interface 300 of the pet insurance system. The user interface may include a status bar 302 that shows statistics about the system (enrollments, certificates, claims and claims paid), a pet status portion 304 for each pet that is part of the pet insurance system and a navigation portion 306 that allows the user to navigate around the pet insurance system. The user interface may have are area 308 for each pet wherein that area further has start claim button 310 that allows the pet hospital to start an insurance claim on behalf of the pet owner for the particular pet and a status indicator 312, known as a Paw Print, that indicates a status of the pet within the pet insurance system. The generation of the Paw Print and the information that it conveys is described below in more detail.

Figure 4:
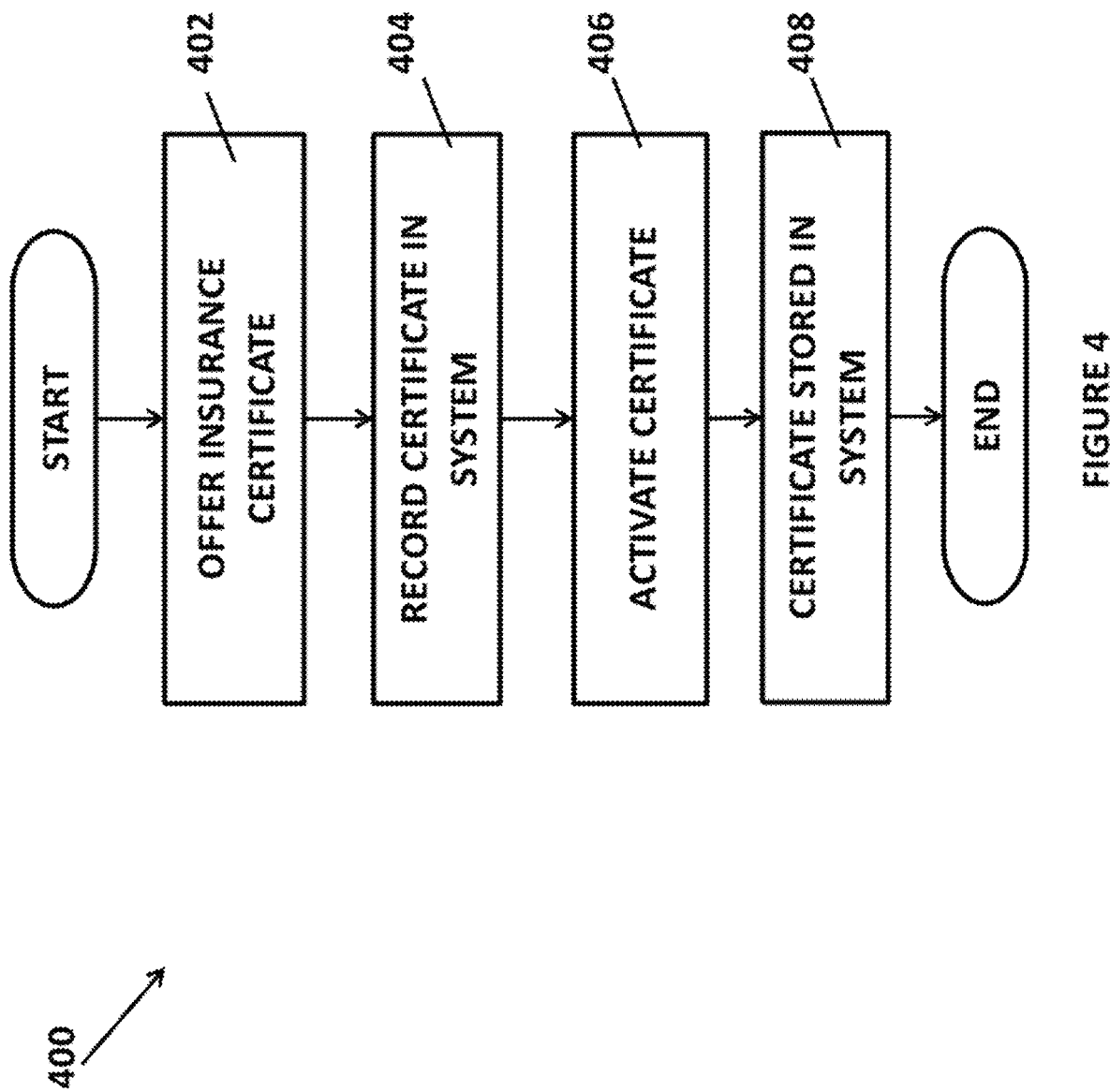
FIG. 4 illustrates a method for obtaining insurance and certificate tracking using the pet insurance system.
Figure 5:
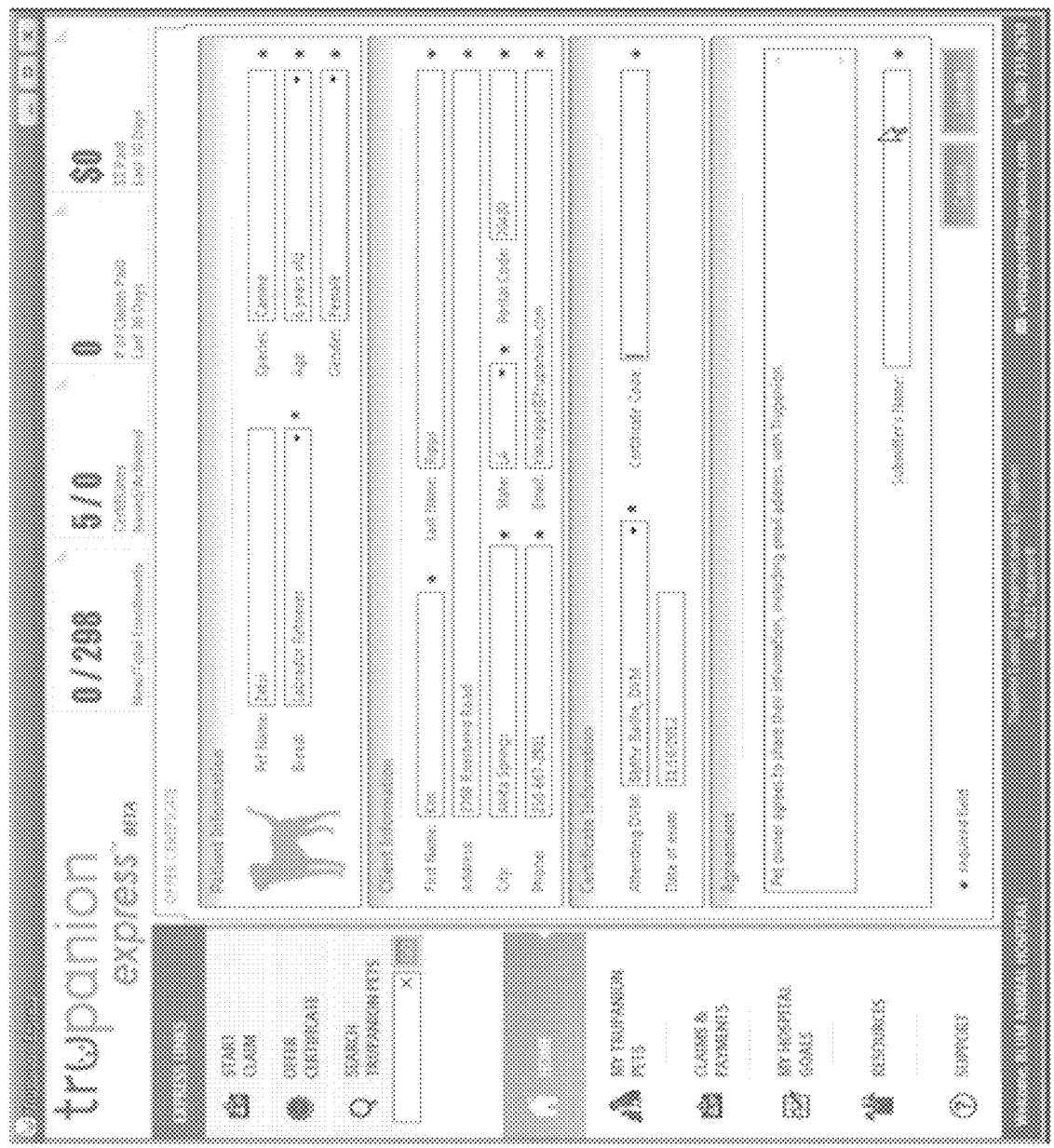
FIG. 5 illustrates an example of a user interface for offering a pet insurance certificate to a pet owner.

FIG. 4 illustrates a method 400 for obtaining insurance and certificate tracking using the pet insurance system and FIG. 5 illustrates an example of a user interface for offering a pet insurance certificate to a pet owner. The pet insurance system makes it easier for a pet owner to get pet insurance (assuming no pre-existing conditions that prevent it) and then quickly be able to have proof of the pet insurance in the form of a certificate that can be presented to the veterinary practice or pet hospital to establish the insurance of the pet. In the method, a doctor may offer a pet owner a certificate (402) for pet insurance for a particular pet through the express service component 204. When the doctor offers the insurance to the pet owner, a person at the veterinary practice or pet hospital may enter the certificate into the client 200 and the information about the certificate (such as shown in FIG. 5) is passed onto the backend component 106 through the Trupanion express service 204. The pet owner, using a computing device 102 may then activate the certificate (and obtain pet insurance) using an email link of by phone which is sent to the backend component 204. Once the pet owner activates the certificate, the pet owner receives the certificate of insurance which is also passed back to the veterinary practice or pet hospital through the express service component 204 so that the veterinary practice or pet hospital receive quick notice of the insurance for the pet. In addition, since the computing device 104 and the backend component 106 are integrated together as shown in FIG. 2, everyone involved in the pet insurance is rapidly notified of the insurance. For example, this means that the veterinary practice or pet hospital can be comfortable that the pet has insurance for the procedure that is about to be performed.

In addition to the process above, the system also allows the veterinary practice or pet hospital, when they want to perform a procedure or treatment, to pre-approve a pet for the treatment or procedure using a pre-approval request made through the client 200 and the express service 204 that communicates the pre-approval request to the backend component 106. In this pre-approval, the Paw Print has not been generated for the pet so it is not typically used during the pre-approval process.

Figure 6:
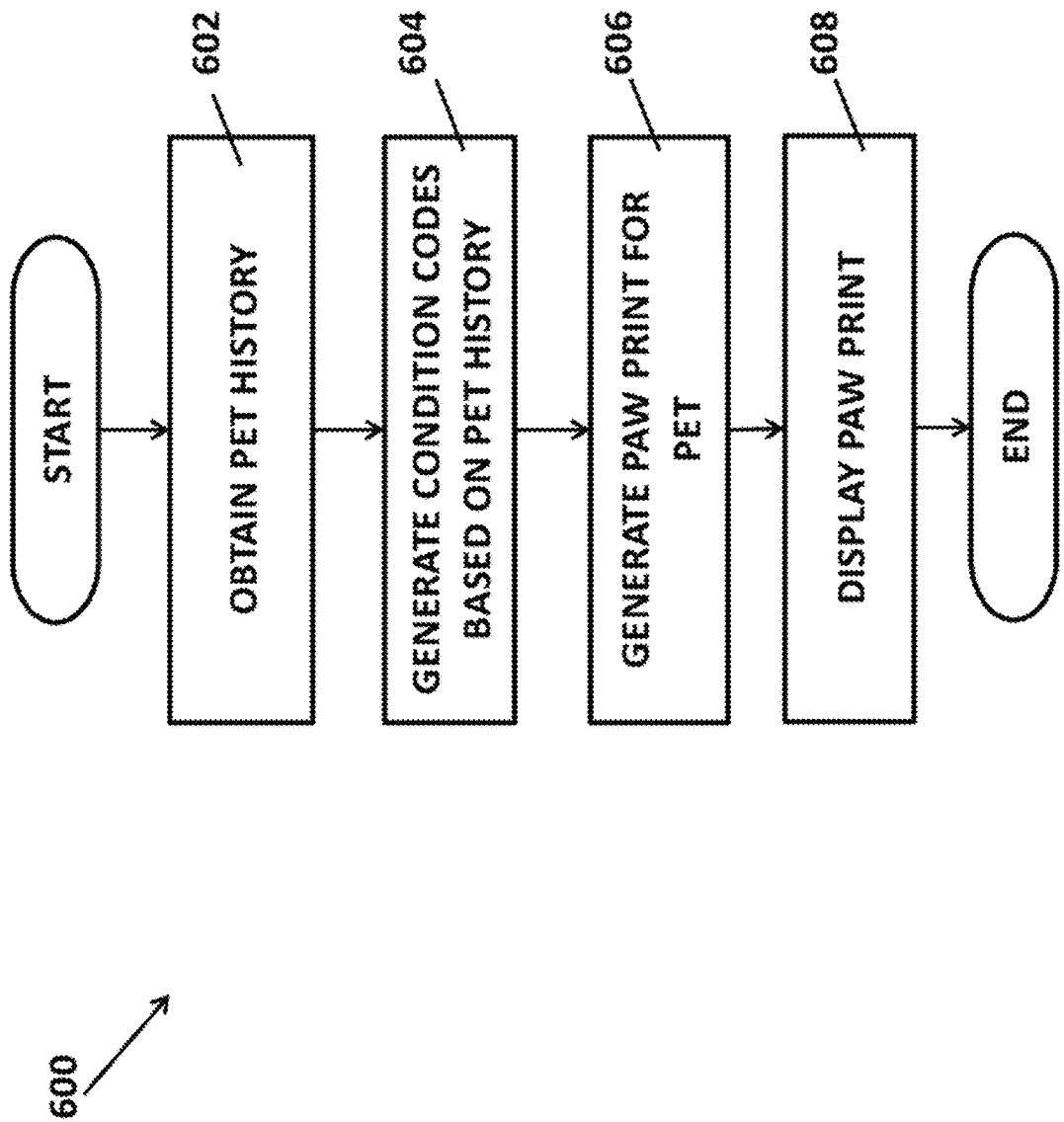
FIG. 6 illustrates a method for determining and displaying a status of a pet to users of the pet insurance system.
Figure 7:
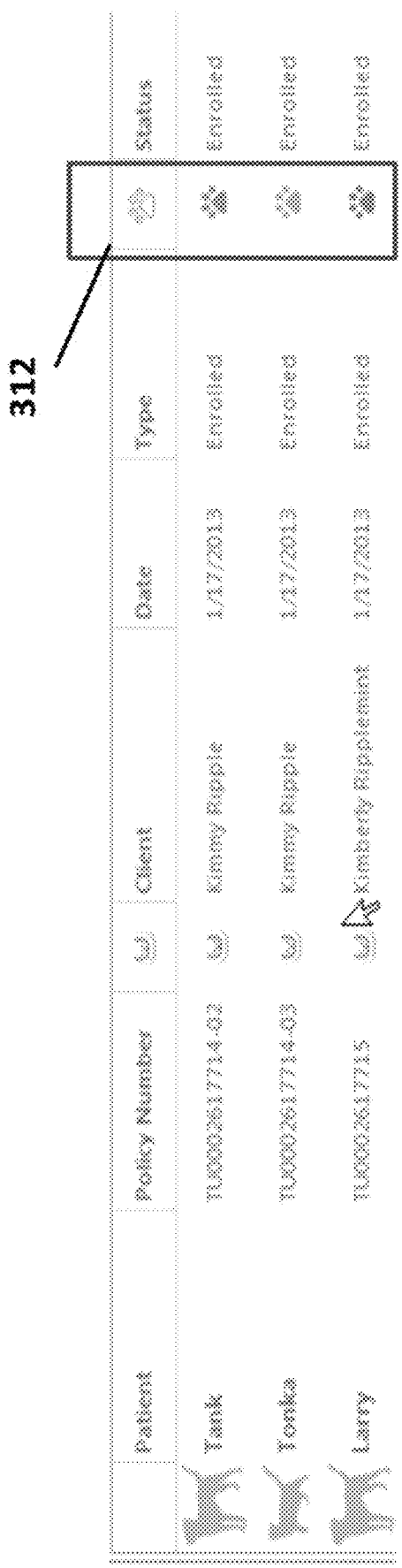
FIG. 7 illustrates an example of a user interface of the pet insurance system that displays a status of each pet.
Figure 8:
FIG. 8 illustrates an example of a user interface that displays a set of details of the status of a pet.

FIG. 6 illustrates a method 600 for determining and displaying a status of a pet to users of the pet insurance system. When a pet owner is trying to get insurance for a pet or at any other time once the pet is the process of or has obtained insurance, the system displays the status indicator 312 for the pet as shown in FIG. 7. The status indicator for each pet may be color coded so that a doctor/employee at the veterinary practice or pet hospital can quickly determine the status of the pet. For example, the status indicator may be a green color indicating that the pet has no pre-existing condition, may be an orange color indicating that the pet does have one or more pre-existing conditions and may be a grey color indicating that the generation of the status indicator is in process for the particular pet. In addition to the status indicator, the user may click on the status identifier and see the additional details about the pet in a user interface like that shown in FIG. 8.

Returning to FIG. 6, when the pet insurance system is generating the status indicator, the backend component 104 (and the enrollment processing system 212) may obtain a history of the pet from any veterinary practice or pet hospital that has seen the pet in the past though the Trupanion express service 204 (602). The system may then generate condition codes based on the pet history (604) and then generate the appropriate status indicator (Paw Print) based on the condition codes (606). The system may then display the status indicators to the users of the system (608) which allows all of the users to rapidly see the status for a pet in a user interface. For a veterinary practice or pet hospital, the status indicator allows, for example, the doctor to quickly determine whether or not a to be performed procedure will be covered by the insurance and then make treatment decisions based on the status indicator. Since the backend component 106 and each computing device 104 in each veterinary practice or pet hospital are integrated as shown in FIG. 2, the status indicator may be propagated to all of the users of the system quickly.

Figure 9A:
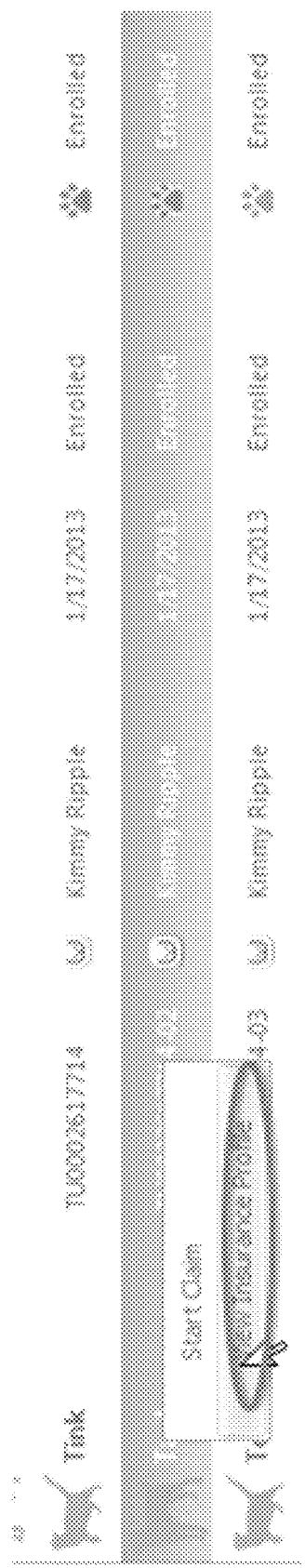
FIGS. 9A and 9B illustrates examples of user interfaces to view an insurance profile of a pet.
Figure 9B:

FIGS. 9A and 9B illustrates examples of user interfaces to view an insurance profile of a pet. This allows a user of the system (a pet owner or veterinary practice or pet hospital) to quickly view the insurance summary for a pet.

Figure 10:
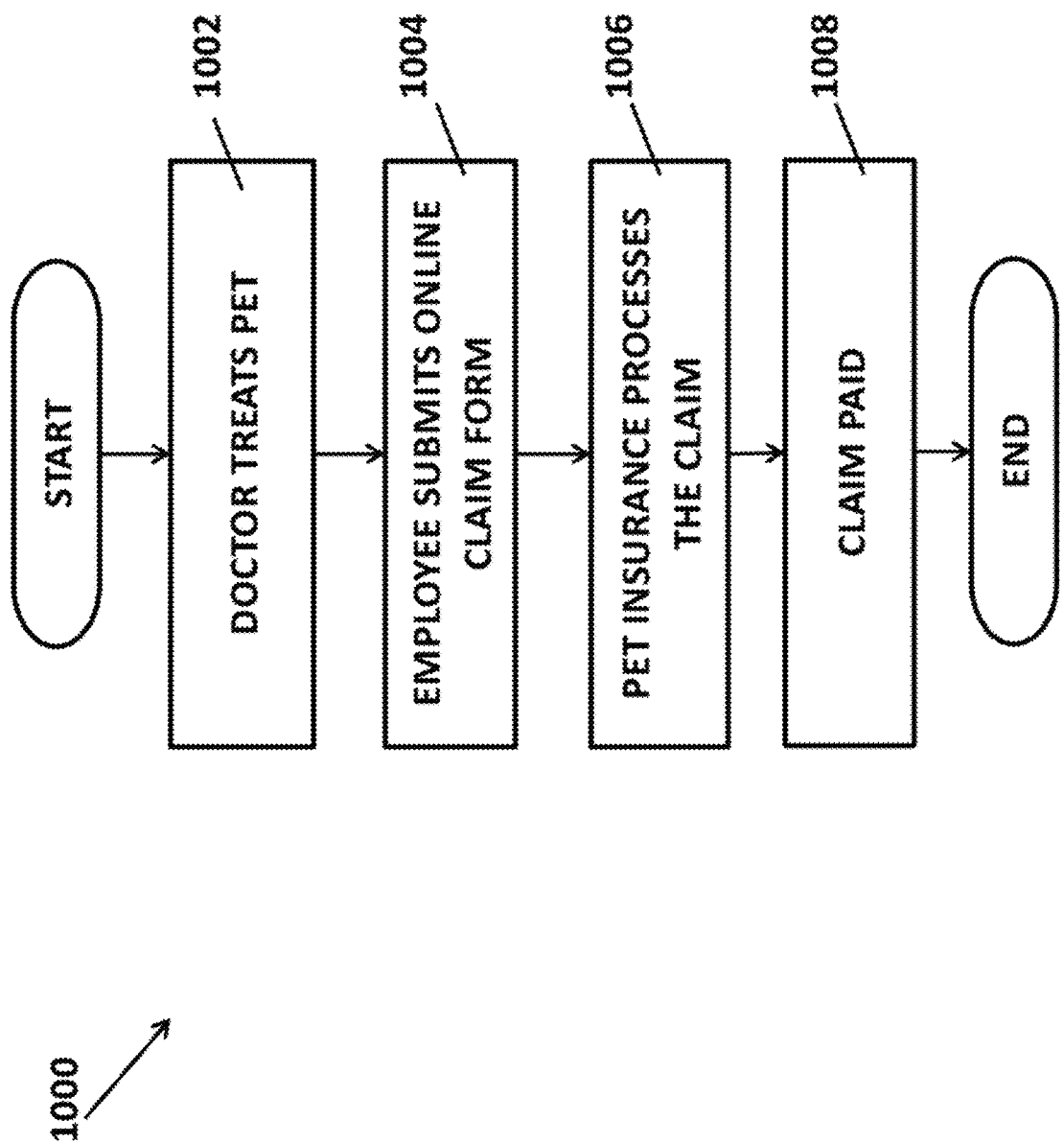
FIG. 10 illustrates a method for submitting and processing a claim in the pet insurance system.
Figure 11:
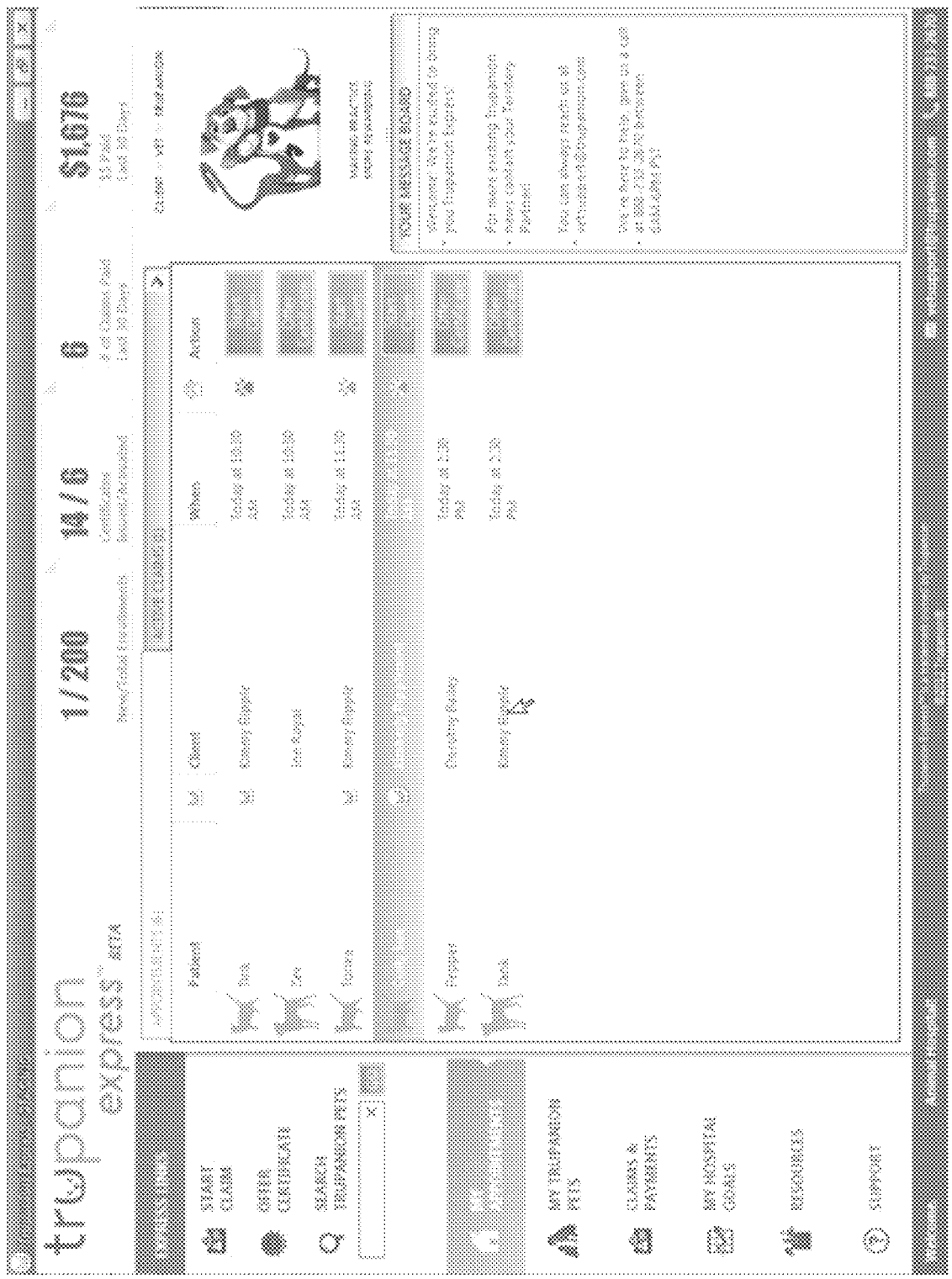
FIG. 11 illustrates an example of a user interface of submitting a claim in the pet insurance system.
Figure 12:
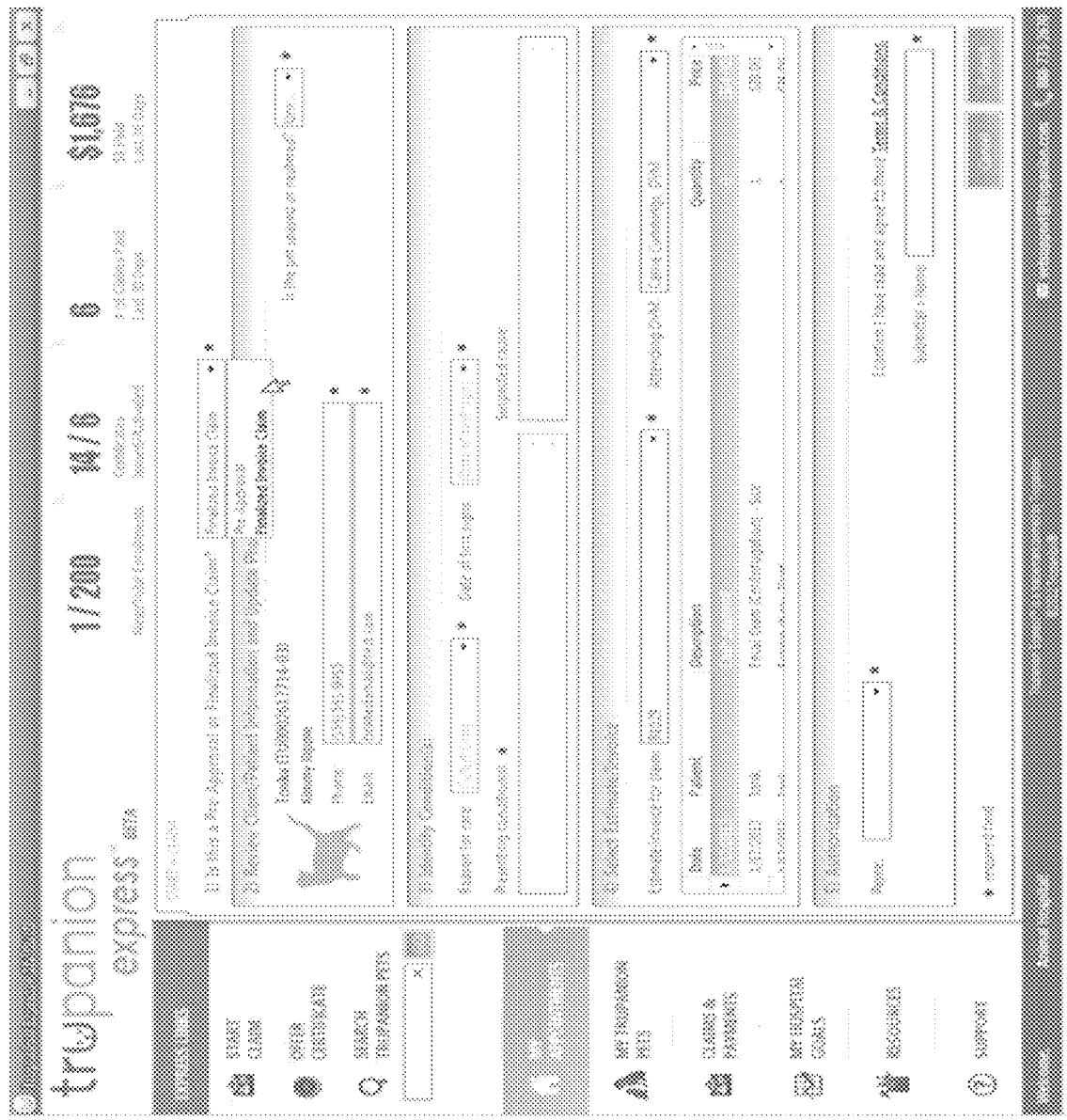
FIG. 12 illustrates an example of a claims form in the pet insurance system.

FIG. 10 illustrates a method 100 for submitting and processing a claim in the pet insurance system. Since the backend component 106 and each computing device 104 in each veterinary practice or pet hospital are integrated as shown in FIG. 2 and the system generate the pet Paw Print which indicated pre-existing conditions that might affect an insurance claim, an insurance claim may be quickly processed by the claim processing portion 214. A claim starts when a doctor treats a pet (1002) and the doctor/employee of the doctor creates and submit a claim (see for example FIG. 11) for the treatment using a claim form (such as shown in FIG. 12) (1004) that is generated by the client 200 in combination with the express service 204. The pet insurance company (through the claim processing system 214) may then process the claim. The pet insurance company has the status of the pet's health history (based on the Paw Print) already stored in the system and thus is able to quickly approve or deny the insurance claim for the pet (1006.) If the claim is approved, the claim may be paid (1008) directly to the veterinary practice or pet hospital (in one implementation, electronically via ACH) and then the pet owner pays their portion to the pet hospital. In this manner, the system allows a claim to be quickly processed and then paid if the insurance claim is approved.

Figure 13:
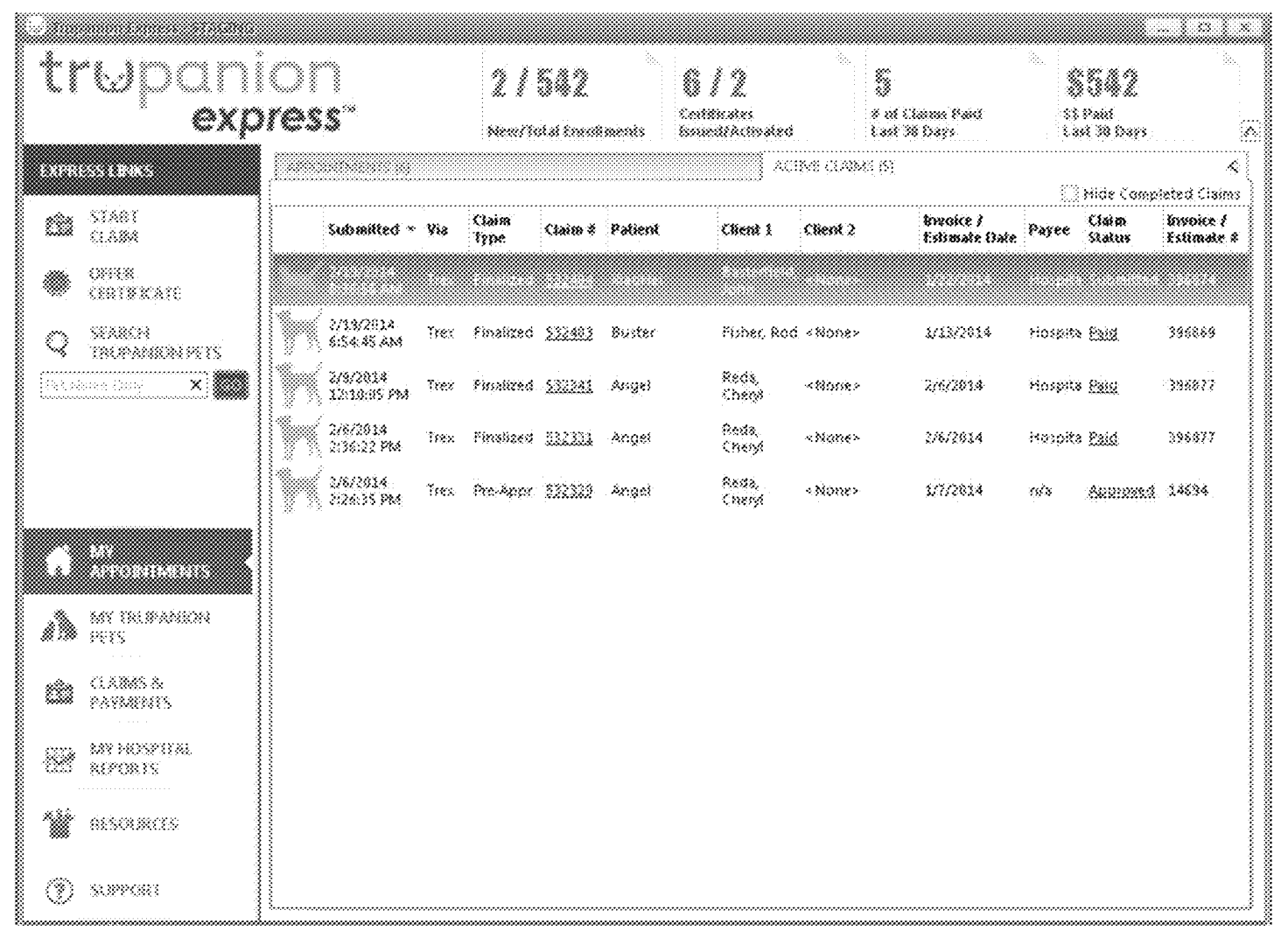
Figures 14A, 14B:
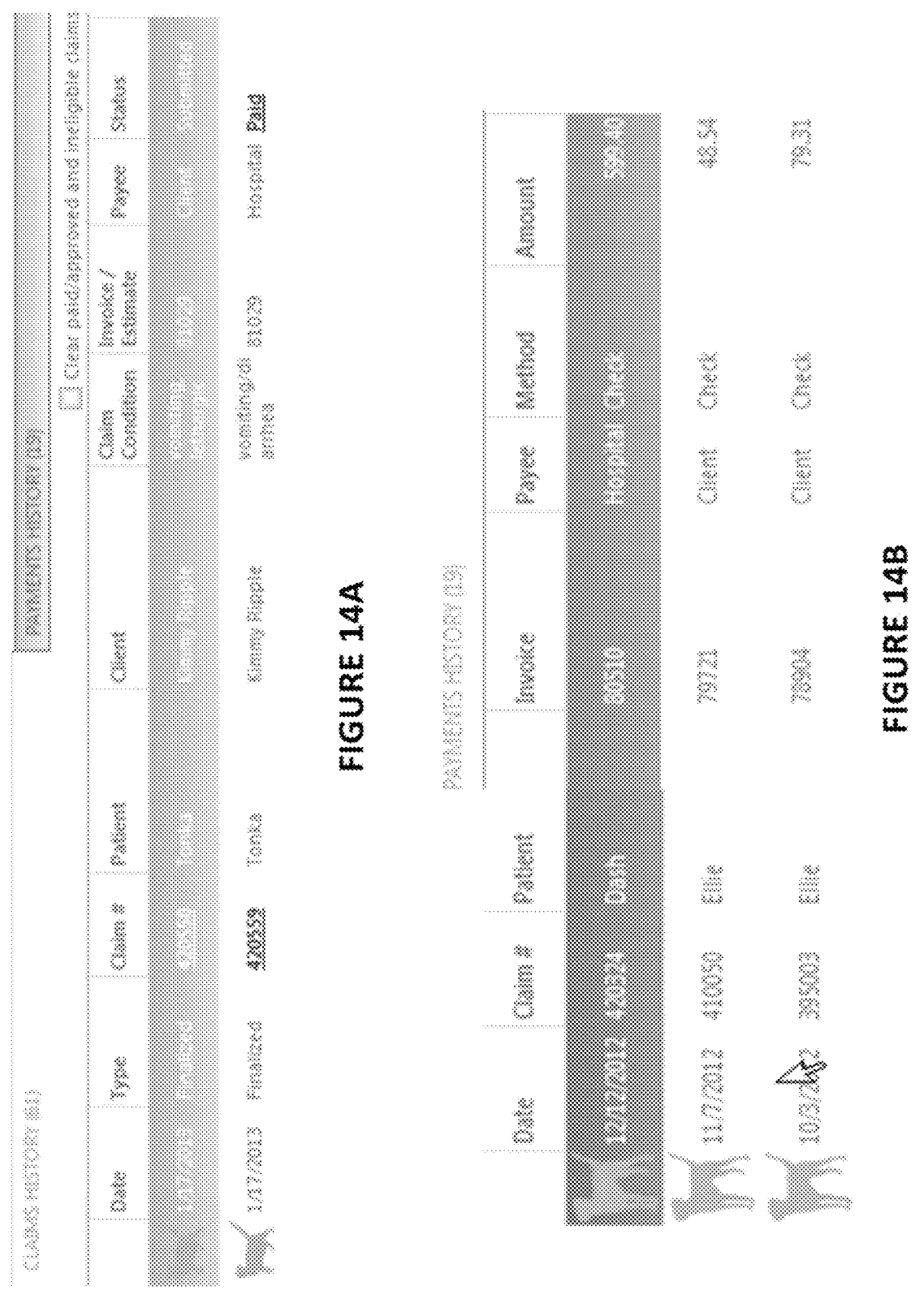

FIG. 13 illustrates an example of a claims submission user interface of the pet insurance system 100 that allows user to see current claims and the status of those claims. FIGS. 14A and 14B are examples of a new claims and claim payment user interface of the pet insurance system.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A method for generating pet status indicator, comprising:
   providing a plurality of pet insurance components, each integrated into one of a plurality of veterinary practices, the veterinary practices each having one of a plurality of practice management systems that each stores one of a plurality of portions of a medical history of an animal being treated by the veterinary practice;
   obtaining data from each of the practice management systems at the plurality of veterinary practices, using the pet insurance component, the data including the plurality of portions of medical history of the animal being treated;

mapping data from a first of the plurality of practice management systems a first of the veterinary practices to the remote pet insurance system by a plug-and-play express system connected to the first practice system and in communication with the backend component, the plug-and-play express system:
  receiving data from a first of the plurality of practice management systems;
  mapping the data according to the remote pet insurance system; and
  sending the mapped data to the remote pet insurance system, thereby limiting the data traffic between the remote pet insurance system and first of the plurality of practice management systems to create efficient correspondence between the remote pet insurance system and first of the plurality of practice management systems and improve the enrollment processing of the animal, the plug-and-play express system being plug-and-play integratable with a second or more of the plurality of practice management systems for connection thereto;
storing the medical history for the animal being treated at the remote pet insurance system having a processor, a memory and a plurality of lines of computer instructions;
generating, by the pet insurance system, one or more condition codes based on the medical history of the animal being treated, each condition code indicating a pre-existing condition of the animal based on the medical history of the animal;
generating, by the pet insurance system based on the one or more condition codes, a Paw Print for the animal, the Paw Print being color coded to indicate the animal having no pre-existing conditions, the animal having one or more pre-existing conditions and a pending status;
communicating, through the pet insurance component, the Paw Print from the animal being treated to the veterinary practice; and
displaying, at the veterinary practice, the generated Paw Print for the animal to an employee of the veterinary practice so that the employee visually determines an insurance status of the animal.

2. The method of claim 1 further comprising displaying the Paw Print of the animal to a veterinarian that is treating the animal.

3. The method of claim 1 wherein the Paw Print for the animal having no pre-existing conditions is green, the Paw Print for the animal having one or more pre-existing conditions is orange and the Paw Print for the pending status is grey.

\* \* \* \* \*